(12) United States Patent
Kiefer et al.

(10) Patent No.: US 7,482,174 B2
(45) Date of Patent: Jan. 27, 2009

(54) DISEASE MARKERS FOR EARLY STAGE ATHEROSCLEROSIS

(75) Inventors: Charles R. Kiefer, Shrewsbury, MA (US); L. Michael Snyder, Framingham, MA (US); James B. McKenney, Hubbardston, MA (US); Jane F. Trainor, Webster, MA (US)

(73) Assignee: University of Massachusetts, Boston, MA (US)

( * ) Notice: Subject to any disclaimer, the term of this patent is extended or adjusted under 35 U.S.C. 154(b) by 55 days.

(21) Appl. No.: 11/220,818

(22) Filed: Sep. 7, 2005

(65) Prior Publication Data

US 2006/0057642 A1 Mar. 16, 2006

Related U.S. Application Data

(60) Provisional application No. 60/608,199, filed on Sep. 9, 2004.

(51) Int. Cl.
G01N 33/53 (2006.01)
(52) U.S. Cl. ........................ 436/811; 436/501; 435/7.92; 435/7.93; 435/7.94
(58) Field of Classification Search ..................... 435/6, 435/7.1, 7.92–7.95; 436/501, 518, 525–528, 436/164, 811; 204/450, 456
See application file for complete search history.

(56) References Cited

U.S. PATENT DOCUMENTS

| 6,040,147 A * | 3/2000 | Ridker et al. ............... 435/7.24 |
| 2003/0130228 A1 | 7/2003 | Chen |
| 2003/0143223 A1 | 7/2003 | Cabezas et al. |
| 2005/0153377 A1* | 7/2005 | Tamura et al. ............. 435/7.92 |

OTHER PUBLICATIONS

Strong et al., Prevalence and Extent of Atherosclerosis in Adolescents and Young Adults, JAMA Feb. 24, 1999, vol. 281, No. 8, pp. 727-735.*
Ridker et al., Novel Risk Factors for Systemic Atherosclerosis, JAMA, May 16, 2001, vol. 285, No. 19, pp. 2481-2485.*
Maggio et al., Enzyme-Immunoassay, CRC Press Inc. 1987, pp. 186-187).*
Elgharib et al, C-reactive protein as a novel biomarker, Postgraduate Medicine, vol. 114, No. 6, Dec. 2003.*
LaPerna et al., Diagnosis and medical management of patients with intermittent claudication, JAOA, vol. 100, No. 10, Supplement to Oct. 2000, pp. S10-S14.*
Ablij et al., "C-reactive protein: history and revival," Eur. J. Intern. Med., 13:412-422 (2002).
Ledue et al., "High Sensitivity Immunoassays for C-Reactive Protein: Promises and Pitfalls," Clin. Chem. Lab. Med., 39(11):1171-1176 (2001).
Ruleva et al., "Structure of C-reactive Protein Excreted in Urine during Acute Rejection Episodes," Bull. Exp. Biol. Med., 135(3):250-252 (2003).

Baszczynski et al., "Epidemiology of risk factors of atherosclerosis and preventative program for youth" Int. Angiol. 9(1):20-21 (1990) Abstract only.
Ji et al., "Cell membranes and liposomes dissociate C-reactive protein (CRP) to form a new, biologically active structural intermediate: mCRPm," FASEB J. 21:284-294 (2007).
Kanai et al., "Real-time velocimetry for evaluation of change in thickness of arterial wall" Ultrasonics 38(1-8):381-386 (2000) Abstract only.
Blake and Ridker, "Study of the spontaneous dissociation of rabbit C-reactive protein," Arterio. Thromb. Vasc. Biol., 22:1512-1513 (2002).
Bobryshev and Lord, "Accumulation of co-localised unesterified cholesterol and neutral lipids within vacuolised elastin fibres in athero-prone areas of the human aorta," Atherosclerosis, 142:121-131 (1999).
Kiefer et al., "Maturation-Dependent Acquired Coronary Structural Alterations and Atherogenesis in the Dahl Sodium-Sensitive Hypertensive Rat," Circulation, 106:2486-2490 (2002).
Kiefer et al., "Pulse pressure-driven neutral lipid accumulation and correlative proinflammatory markers of accelerated atherogenesis," Atherosclerosis 183:17-24 (2005).
Khreiss et al., "Opposing Effects of C-Reactive Protein Isoforms on Shear-Induced Neutrophil-Platelet Adhesion and Neutrophil Aggregation in Whole Blood," Circulation, 110:2713-2720 (2004).
Kim et al., "Opsonization of Apoptotic Cells and Its Effect on Macrophage and T Cell Immune Responses," Ann. N.Y. Acad. Sci., 987:68-78 (2003).
Kresl et al., "Conversion of native oligomeric to a modified monomeric form of human C-reactive protein," Int. J. Biochem. Cell Biol., 30(12):1415-26 (1998).
Rassouli et al., "Derivation of the Amino Acid Sequence of Rat C-reactive Protein from cDNA Cloning with Additional Studies on the Nature of Its Dimeric Component," J. Biol. Chem., 267:2947-2954 (1992).
Ridker et al., "Clinical Application of C-Reactive Protein for Cardiovascular Disease Detection and Prevention," Circulation, 107:363-369 (2003).
Schmermund and Erbel, "Unstable Coronary Plaque and Its Relation to Coronary Calcium," Circulation, 104:1682-1687 (2001).
Schwedler et al., "Native C-Reactive Protein Increases Whereas Modified C-Reactive Protein Reduces Atherosclerosis in Apolipoprotein E-Knockout Mice," 112(7):1016 (2005).
Thompson et al., "The physiological structure of human C-reactive protein and its complex with Phosphocholine," Structure, 7:169-177 (1999).
Vaith et al., "Complement activation by C-reactive protein on the HEp-2 cell substrate," Int. Arch. Allergy Immunol., 111(2):107-17 (1996).
Volanakis and Wirtz, "Interaction of C-reactive protein with artificial phosphatidylcholine bilayers," Nature, 281:155-157 (1979).
Wang and Sui, "Dissociation and Subunit Rearrangement of Membrane-Bound Human C-Reactive Proteins," Biochem. Biophys. Res. Comm., 288:75-79 (2001).
Wu et al., "Study of the spontaneous dissociation of rabbit C-reactive protein," Biochem. (Moscow), 67:1377-1382 (2002).

* cited by examiner

*Primary Examiner*—Mark L Shibuya
*Assistant Examiner*—Gary W Counts
(74) *Attorney, Agent, or Firm*—Fish & Richardson P.C.

(57) ABSTRACT

The invention relates to methods of diagnosing early stages of atherosclerosis.

15 Claims, 3 Drawing Sheets

US 7,482,174 B2

DISEASE MARKERS FOR EARLY STAGE ATHEROSCLEROSIS

CLAIM OF PRIORITY

This application claims priority under 35 USC §119(e) to U.S. Provisional Patent Application Ser. No. 60/608,199, filed on Sep. 9, 2004, the entire contents of which are hereby incorporated by reference.

TECHNICAL FIELD

This invention relates to methods of diagnosing early stages of atherosclerosis.

BACKGROUND

Native C-reactive protein (CRP), a marker of inflammation that is a planar pentameric arrangement of five identical 23 kDa subunits, exhibits calcium-dependent binding to phosphorylcholine (PC) and has been demonstrated to interact with artificial PC bilayers, although a disturbance of the bilayer organization is required (Volanakis and Wirtz, Nature, 281:155-157 (1979)). In vivo, endothelial apoptotic processes culminate in exposure of phosphorylcholine groups on the membrane surface and capture of circulating native CRP (Kim et al. Ann NY Acad. Sci. 987:68-78 (2003)). Once bound to PC, the pentameric ring of the human CRP opens, resulting in dissociation of the subunits into monomeric (single subunit) forms (Wang and Sui, Biochem. Biophys. Res. Comm., 288:75-79 (2001)).

Total CRP levels have been shown in multiple prospective epidemiological studies to predict future cardiovascular disease, including myocardial infarction, stroke, peripheral arterial disease, sudden cardiac death and cardiovascular events in general (Ridker, Circulation, 107:363-369 (2003)).

SUMMARY

The present invention is based, in part, on the discovery that elevated serum levels of free monomeric C-reactive protein (mCRP) precede the accumulation of pooled neutral lipid in the arterial wall, providing a serum diagnostic marker for early pathologic changes. Thus, this marker can be used to predict and/or detect the onset of subclinical inflammatory damage to arteries or organs in general, e.g., atherosclerosis at a very early stage.

In general, the invention provides methods of diagnosing a subject with early stage atherosclerosis. The methods include providing a sample from the subject, e.g., a bodily fluid such as serum; determining the level of monomeric C-reactive protein (mCRP) in the sample; and comparing the level of mCRP in the sample with a predetermined value, e.g., a level of mCRP in a healthy control, e.g., an age and/or gender-matched subject. The presence of mCRP in the sample at levels above those of the predetermined value indicate that the subject has early stage atherosclerosis. In some embodiments, the predetermined value is a range of levels between about 0.3 to 0.5 mg/L (13-21 nmol/L) in the sample.

A "subject," as used herein, is a mammal, e.g., a human. For example, a subject can be an adolescent human, a preadolescent human, or a human in late childhood. As used herein, "adolescent" means age 12-20 (female), 13-21 (male); "preadolescent" means age 10-12 (female), 11-13 (male); and "late childhood" means about age 6—preadolescence. In some embodiments, the subject has a risk factor for the development of early stage atherosclerosis, e.g., elevated serum LDL-cholesterol levels; elevated pulse pressure; family history; smoking history; diabetes mellitus; dyslipidemia; hypertension; a family history of premature atherosclerosis; and/or hyperhomocystinemia.

In some embodiments, the subject has intermittent claudication and/or rest pain. In other embodiments, the subject has neither intermittent claudication nor rest pain.

The methods described herein can also include administering a treatment, e.g., diet modification; exercise modification; administration of an antiplatelet agent; administration of a cholesterol lowering agent; and/or administration of an antihypertensive agent, to the subject, where mCRP is present in the sample at levels above those of a predetermined value.

The present invention also provides other methods of diagnosing a subject with early stage atherosclerosis. These methods include providing a sample from the subject, e.g., a bodily fluid such as serum; determining a level of total C-reactive protein (CRP) in the sample; determining the level of monomeric C-reactive protein (mCRP) in the sample; calculating the ratio of monomeric CRP to total CRP, and optionally comparing the ratio of mCRP:total CRP in the sample with a predetermined value, e.g., a ratio of mCRP:total CRP in a healthy control subject, e.g., an age and/or gender-matched subject. A ratio of mCRP:total CRP in the sample at levels above those of the predetermined value indicate that the subject has early stage atherosclerosis. In some embodiments, the predetermined value is a ratio of 0.23. "Total CRP" in humans includes all molecular forms of CRP, e.g., pentameric (native) forms, monomeric (single subunit) forms, monomeric fragments, or any aggregation of native pentamers, subunits, or subunit fragments with themselves or with each other. In rats, total CRP includes dimers as well.

Also provided are additional methods of diagnosing a subject with early stage atherosclerosis. The methods include providing a sample from the subject, e.g., a bodily fluid such as serum; determining a level of pentameric C-reactive protein (pCRP) in the sample; determining the level of monomeric C-reactive protein (mCRP) in the sample; calculating the ratio of monomeric CRP to pentameric CRP (mCRP:pCRP), and optionally comparing the ratio of mCRP:pCRP in the sample with a predetermined value, e.g., a ratio of mCRP:pCRP in a healthy control subject, e.g., an age and/or gender-matched subject. A ratio of mCRP:pCRP in the sample at levels above those of the predetermined value indicate that the subject has early stage atherosclerosis. A "critical value" is a level that is significantly above or below the standard range of normal values for that analyte in healthy individuals (in some embodiments, calculated as ±2 SD from the mean). A level above the critical value generally suggests a serious medical condition that may require immediate medical attention for the patient. In some embodiments, the predetermined value is a ratio of about 1.0, and ratios significantly below about 1.0 are subcritical, while ratios significantly above about 1.0 are critical.

In some embodiments, the methods include administering a treatment, e.g., diet modification; exercise modification; administration of an antiplatelet agent; administration of a cholesterol lowering agent; and/or administration of an antihypertensive agent, to the subject, if one or more of a level of mCRP, a ratio of mCRP:total CRP, or a ratio of mCRP:pCRP, is above those of the predetermined value.

Also included are methods of evaluating the efficacy of a treatment for atherosclerosis, e.g., early stage atherosclerosis. The methods include administering a treatment to a subject and evaluating an effect of the treatment on one or more of mCRP levels, the ratio of mCRP:total CRP, or the ratio of mCRP:pCRP. In some embodiments, the methods further include determining one or more of mCRP levels, the ratio of mCRP:total CRP, or the ratio of mCRP:pCRP in the subject before the treatment is administered, e.g., to establish a baseline in the subject. A treatment that causes a decrease in one or more of mCRP levels, the ratio of mCRP:total CRP, or the ratio of mCRP:pCRP can be considered effective in treating early-stage atherosclerosis. The treatment can be, e.g., an experimental treatment, or a known treatment that has not been previously administered to the subject. The treatment can be intended to treat early stage atherosclerosis in the subject. Alternatively, the treatment can be intended to treat another condition, and the present methods can be used to evaluate potential beneficial or detrimental side effects on early-stage atherosclerosis or risk of developing atherosclerosis.

In some embodiments, the methods described herein also include determining the level of oxidized low-density lipoprotein (LDL) in the sample, and comparing it to a predetermined value level of oxLDL, e.g., a level in a normal, age-matched, healthy control subject.

Further, the invention provides kits for carrying out the methods described herein. For example, the invention includes kits for use in a method of capturing and concentrating total CRP. The kits will generally include a calcium supplementation buffer, a rinse buffer, a release buffer, and instructions for carrying out the method. Optionally, the kit can also include phosphorylcholine beads.

The invention provides several advantages. Because mCRP levels are diagnostic of the very earliest, preclinical stages of the development of atherosclerosis, treatment of individuals identified by the diagnostic methods described herein is likely to be far more effective than treatment begun when symptoms have begun to appear, which may prevent the subsequent development of full-blown atherosclerosis altogether. In this respect, the methods described herein can be used to identify individuals who are in the process of developing atherosclerosis before any symptoms have arisen, symptoms which are at best uncomfortable and at worst painful and life-threatening, and can eliminate the need for surgical intervention in later life. In addition, milder forms of treatment can be used, such as altering diet and exercise regimens and/or administering anti-hypertensive therapy, with a greater likelihood of success than in subjects with more advanced disease.

Also described herein is an animal model of early-stage atherosclerosis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, database entries, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
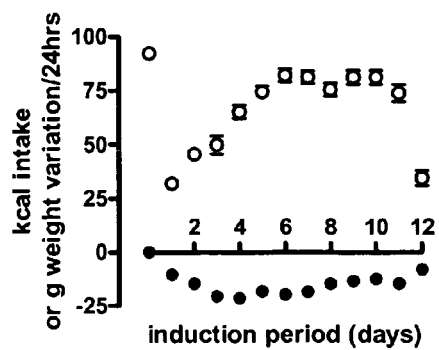
FIG. 1 is a graph illustrating caloric intake and weight change in rats over a twelve day induction period. ○, mean (SE) kcal intake/24 hours. ●, mean (SE) weight variation from baseline in g/24 hours. Single group, N=17.

The present invention relates to the discovery that elevated serum levels of free monomeric C-reactive protein (mCRP) and oxLDL precede and track, respectively, the accumulation of pooled neutral lipid in the arterial wall matrix, thus providing serum markers for early histopathologic changes.

The accumulation of neutral lipid in the arterial matrix is associated with degenerating elastin fibers in the pre-atherosclerotic stage (Bobryshev and Lord, Atherosclerosis, 142: 121-131 (1999)). In humans, such a preclinical stage should be the most readily reversible stage of the disease (e.g., by dietary modification and/or hypertensive therapy), as it precedes the arrival of monocytes, their entry into the arterial wall, and their conversion to the more pathologic foam cells that drive subsequent stages of the disease.

Detecting Monomeric C-Reactive Protein

The methods described herein include detecting levels of monomeric C-reactive protein (mCRP), and, optionally, total CRP and/or pentameric CRP (pCRP), in a sample from a subject. The level can be obtained by any art recognized method. Typically, the level is determined by measuring the level of the marker in a body fluid, for example, blood, lymph, saliva, urine and the like. The level can be determined by ELISA, or immunoassays or other conventional techniques for determining the presence of the marker. Conventional methods include sending samples of a patient's body fluid to a commercial laboratory for measurement. In some embodiments, the level is obtained by measuring the total quantity of marker in a specific volume of a body fluid, for example, blood, lymph, saliva, urine, and the like; in some embodiments, the methods include dividing the amount of mCRP detected by the quantity of fluid in the sample, to give a level in amount per volume (e.g., mg/L).

Quantities of mCRP can be measured directly, e.g., using a detection technique with sufficient sensitivity and specificity to measure the very low levels of mCRP that would be expected in subjects with early stage, preclinical atherosclerosis. Methods are known in the art for measuring low levels of analytes and can be applied to the measurement of mCRP, including mass spectrometry; matrix assisted laser desorption/ionization time of flight (MALDI-TOF); and capillary electrophoresis. In general, the CRP in a sample must first be captured and concentrated, e.g., using standard capture and release methods. One exemplary method employs phosphorylcholine (PC)-conjugated agarose beads (Pierce, Rockville, Ill.) to capture substantially all of the CRP molecules (e.g., pentameric and monomeric forms) present in the sample. This can be followed by quantitative analysis of the forms separated by size exclusion chromatography (SEC), using a method such as high performance liquid chromatography (HPLC) incorporating an SEC matrix). Finally, a ratio of forms, e.g., mCRP:pCRP, or mCRP:total CRP, can be calculated.

The methods described herein can be performed manually, or can be completely or partially automated. An exemplary automated assay involves two separate machines: one for total CRP capture and release, and a second for HPLC or similar size-exclusion fractionation and integration of peak areas, e.g., pentameric and monomeric peak areas. The automated capture and release can be, for example, adapted to PC-coated microtiter wells or PC-coated beads. HPLC can then be used to accomplish a rapid yet gentle enough chromatographic separation of pentameric from monomeric CRP. In some embodiments, the method is fully automated, e.g., performed by robotic, computer-controlled machinery. Where pentameric forms are to be measured, it is important to maintain the CRP in a form that is as close to native as possible.

In some embodiments, mCRP capture and measurement is achieved utilizing a matrix, such as a protein array. The array can be, for example, individually-addressable areas on a solid surface, e.g., a "chip," e.g., commercially available protein chips (such as the RS100, PS10 or PS20 ProteinChip® arrays from Ciphergen, Fremont, Calif.). Quantitative analysis of the captured CRP molecules by molecular weight is carried out by an automated array reader, e.g., the Ciphergen ProteinChip® BioMarker System for SELDI methods (U.S. Pat. No. 5,894,063 and 6,579,719; European Patent Number EP 0 700 521 B1).

In some embodiments, the methods include concentrating the CRP in the sample, e.g., during the capture and release procedure.

Predetermined Values

The invention also involves comparing the level of mCRP or ratio in the individual with a predetermined value. The predetermined value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quadrants, the lowest quadrant being individuals with the lowest risk and the highest quadrant being individuals with the highest risk.

The predetermined value can depend upon the particular population selected. For example, an apparently healthy, non-smoker population (no detectable disease and no prior history of a cardiovascular disorder) will have a different 'normal' range of markers of systemic inflammation than will a smoking population or a population the members of which have had a prior cardiovascular disorder. Accordingly, the predetermined values selected may take into account the category in which an individual falls. Appropriate ranges and categories can be selected with no more than routine experimentation by those of ordinary skill in the art.

As described in further detail in Example 5 below, normal (nonpathologic) human mCRP levels would theoretically be estimated to be approximately zero, however, it is likely that there will always be an ultra-low (background) level of mCRP in circulation, resulting from constant low-level tissue damage, i.e., the normal wear-and-tear of human existence, such as bumps and physical exercise. Thus, the threshold range of mCRP for subclinical/earliest stage atherosclerosis is estimated to be between about 0.3 to 0.5 mg/L (13-21 nmol/L). The term "subclinical" refers to a level of pathology above the ultra-low, but below the critical value for clinical pathology (total CRP above 8 mg/L). As described herein, the peak induction (day 8) rat serum was estimated to have 8.2 mg/L pentamer and 2.5 mg/L free monomer, thus totaling 10.7 mg/L total CRP in circulation. Taking the rat mCRP/total CRP ratio at day 8 (2.5/10.7=0.23) as representing a subclinical pathologic state (minimal vascular pathology as indicated by histomorphometric data), and multiplying by the non-pathologic ("normal") range for total human CRP (1.26-1.97 mg/L), gives 0.23×1.26=0.29 mg/L at the low end, and 0.23×1.97=0.45 mg/L of mCRP in serum at the high end of the range of normal values.

Thus, in adolescent, preadolescent, or late childhood human subjects, any detectable level of mCRP can be considered to be pathological. In some embodiments, e.g., in serum samples from post-adolescent subjects, pathologic ranges for subclinical/earliest stage atherosclerosis are above about 0.3 to 0.5 mg/L (13-21 nmol/L). In some embodiments, a pathologic ratio of mCRP:total CRP is above about 0.23. In some embodiments, a pathologic ratio of mCRP:pentameric CRP(pCRP) is above about 1. Levels or ranges above these can be considered indicative of the presence of early stage atherosclerotic processes in a subject.

Atherosclerosis

Atherosclerosis is typically considered a disease of large and medium-sized muscular arteries, characterized by endothelial dysfunction, vascular inflammation, and the accumulation of lipids, cholesterol, calcium, and cellular debris within the intima of the vessel wall. This buildup results in plaque formation, vascular remodeling, acute and chronic luminal obstruction, blood flow abnormalities, and diminished oxygen supply to target organs.

Diet-induced hyperlipidemia, and especially elevation of LDL-cholesterol (LDL), is a major causative factor for the development of atherosclerosis (Woolf, Atherosclerosis Reviews, 18:25-48 (1988); Steinberg, Atherosclerosis Reviews, 18:1-23 (1988); Chapman et al., Eur. Heart J., 19 Suppl. A:A24-30 (1998)). Moreover, the case has been made that it is a sufficient cause, both hypothetically (Steinberg (1988) supra; Williams and Tabas, Arterioscler. Thromb. Vasc. Biol., 15:551-561 (1995)) and empirically in a primate model (Faggiotto et al., Arteriosclerosis, 4:323-340 (1984)). In this paradigm, an increase in plasma levels of LDL, especially the small dense LDL particles (Chapman et al., (1998) supra), leads by simple mass action to their entrapment and retention in the proteoglycan-rich extracellular matrix of the arterial intima, where the multistep process of atherosclerosis actually begins (Camejo et al., Atherosclerosis Supplements, 3:3-9 (2002)).

A useful histopathologic staging system has been provided by the American Heart Association (AHA) based on the classification proposed by Herbert C. Stary (Stary et al., Circulation, 92:1355-1374 (1995); Stary et al., Circulation, 89:2462-2478 (1994); Stary et al., Circulation, 85:391-405 (1992)).

Initial (type I) lesions contain enough atherogenic lipoprotein to elicit an increase in macrophages and formation of scattered macrophage foam cells. As is also true in more advanced lesions, the changes are typically more marked in arterial regions with adaptive intimal thickening. These adaptive thickenings, which are normal and present at consistent locations in every individual from birth, represent adaptations to local mechanical forces and do not obstruct the lumen.

Type II lesions consist primarily of layers of macrophage foam cells and lipid-laden smooth muscle cells; Type II includes lesions commonly known as fatty streaks, which are the result of focal accumulation of serum lipoproteins within the intima of the vessel wall. The fatty streak is observed in the aorta and coronary arteries of most individuals by age 20 years, and is characterized microscopically by lipid-laden macrophages, T lymphocytes, and smooth muscle cells.

Type III lesions are an intermediate stage between type II and type IV. In addition to the lipid-laden cells of type II, type III lesions also contain scattered extracellular clusters of lipid droplets and particles that can disrupt the coherence of intimal smooth muscle cells. Type I-III lesions are typically preclinical (clinically silent or asymptomatic), and are considered to be preclinical and potentially reversible.

The extracellular lipid characteristic of type III lesions is the immediate precursor of the larger, confluent, and more disruptive core of extracellular lipid that distinguishes type IV lesions (atheromas, which are potentially symptom-producing). Beginning around the fourth decade of life, lesions with a lipid core can also contain thick layers of fibrous connective tissue (these are type V lesion) and/or fissure, hematoma, and thrombus (type VI lesion). Type Vb lesions are largely calcified, while type Vc consist primarily of fibrous connective tissue and little or no accumulated lipid or calcium. Elevated serum levels of LDL cholesterol can overwhelm the antioxidant properties of the healthy endothelium, resulting in abnormal endothelial metabolism of this lipid moiety and an increase in levels of oxidized LDL (oxLDL). oxLDL has a wide range of toxic effects, resulting in cell/vessel wall dysfunctions that are associated with the development of atherosclerosis. These dysfunctions include impaired endothelium-dependent dilation and paradoxical vasoconstriction. oxLDL also has a potential role in recritment/retention of monocyte/macrophages (Quinn et al., Proc. Natl. Acad. Sci. USA, 84:2995-2998 (1987)).

The lesions of atherosclerosis do not occur randomly, but are associated with localized hemodynamic factors. Lesions typically form at vessel branch points, e.g., those within the coronary arteries, the major branches of the thoracic and abdominal aorta, and the large conduit vessels of the lower extremities (Reidy and Bowyer, Atherosclerosis, 26:181-194 (1977)). These are regions of marked curvature at areas of geometric irregularity, and where blood undergoes sudden changes in velocity and/or direction of flow. Decreased shear stress resulting from increased turbulence promotes endothelial apoptosis, which is involved in the development of advanced lesions (Freyberg et al., Apoptosis, 6:339-343 (2001)).

Although Types I-III are generally considered "preclinical" (p. 10, lines 14-15), a Type I lesion is generally be the earliest that could be identified by routine histologic methods, primarily by the presence of foam cells. The methods described herein are useful for "pulling" the envelope of staging back to allow detection of disease before it can be identified by traditional histologic typing, by using mCRP to identify pre-histologic events (ie, subtle arterial damage) in atherogenesis. As described herein, analysis of serum marker changes in the rat model is in the pre-Stage I (pre-foam cell) events of atherogenesis demonstrated a change in CRP consumption, as reflected by increased serum mCRP; this is the earliest marker of incipient atherosclerosis that has been identified.

Symptoms

Atherosclerosis typically does not produce symptoms until the lumen of the affected artery is occluded by more than 70%, e.g., type IV-VI lesions. Less severe lesions (type IV-V) are more typically associated with angina, transient ischemic attacks, and claudication/peripheral artery disease, while more severe lesions are associated with myocardial infarction, stroke, critical leg ischemia, and cardiovascular fatality. Symptoms depend on the location of the narrowing or blockage, which can occur almost anywhere in the body, but are typically localized to arteries supplying the brain, kidneys, small intestine, lower extremities, and heart. For example, lesions in the coronary arteries typically manifests as angina; blockage of the coronary arteries can lead to a myocardial infarction, abnormal heart rhythms, and heart failure. Lesions and blockage in the carotid arteries can cause a stroke. Narrowing of the arteries in the limbs, e.g., the legs, can cause intermittent claudication and rest pain. In subjects older than 55, the renal arteries can become narrowed or blocked, sometimes leading to renal failure or malignant hypertension.

Peripheral Atherosclerosis

The two principal symptoms of peripheral atherosclerosis are intermittent claudication and rest pain.

Intermittent claudication is described as discomfort, pain, fatigue, or heaviness felt in the affected extremity during walking, which resolves within a few minutes of resting. Intermittent claudication occurs when the metabolic demand of an exercising muscle exceeds supply, and is caused by a hemodynamically significant stenosis which prevents blood-flow augmentation during exercise. An increased pressure gradient develops across the stenosis and compromises perfusion pressure to the exercising muscle. Ischemia develops, and autoregulatory mechanisms cause local vasodilatation and a further reduction in perfusion pressure. Extravascular forces, created by the exercising muscle, can reduce perfusion pressure even further. The location of the symptom depends on the site of stenosis. Thigh, hip, or buttock claudication may develop in cases of proximal arterial occlusive disease involving the aorta or iliac arteries. Involvement of the femoral and popliteal arteries typically causes calf claudication. Tibial and peroneal artery stenoses may cause pedal claudication.

Rest pain results from failure of the blood supply to adequately meet the basic metabolic requirements of the tissues of the affected extremity, and is typically felt in the toes or foot. The pain is generally initially worse at night time, when the patient is lying in bed with the legs horizontal. Sitting up and dangling the affected leg often alleviates the pain, increasing perfusion pressure via gravitational forces; leg elevation often causes the pain to worsen. Persistent severe ischemia results in skin breakdown, eventually leading to ulceration, necrosis, and gangrene; once this happens, even minor trauma to an ischemic limb can produce a skin lesion that will not heal.

Treatment of Atherosclerosis

The methods described herein include methods for the treatment of atherosclerosis in subjects who have above-normal levels of mCRP, above-normal ratios of mCRP:total CRP, or above-normal ratios of mCRP:pCRP. As used herein, a "treatment" includes any therapeutic or prophylactic intervention that ameliorates, remedies, improves, or prevents or delays the development or progression of, atherosclerosis (including early stage atherosclerosis). In some embodiments, a treatment is administered to a subject who has an above-normal, e.g., pathologic, level of mCRP, ratio of mCRP:total CRP, or ratio of mCRP:pCRP, but who is otherwise free of symptoms calling for an anti-inflammatory agent. In some embodiments, the treatment includes administering an anti-inflammatory agent, alone or in conjunction with another modality for treating, preventing or delaying the development of atherosclerosis, e.g., modification of diet and/or exercise or cessation of smoking.

A number of treatments for atherosclerosis are known in the art. Treatments can include dietary and exercise modifications. For example, the methods can include instructing subjects to maintain a low-fat, low-cholesterol diet, and/or to achieve and maintain ideal body weight through diet and regular aerobic exercise. Subjects who smoke cigarettes can be advised to stop smoking; behavioral and pharmacologic treatment can be used to assist in smoking cessation.

In addition, antiplatelet agents can be administered, including but not limited to aspirin, clopidogrel, ticlopidine, dipyridamole and the glycoprotein IIb/IIIa receptor antagonists (abciximab and tirofiban).

A treatment can also include administering cholesterol-lowering agents such as 3-hydroxy-3-methylglutaryl coenzyme A (HMG-CoA) reductase inhibitors, also known as statins. Statins are also considered to be anti-inflammatory agents (see, e.g., Blake and Ridker, Curr. Control Trials Cardiovasc. Med., 1:161-165 (2000)), and can be used in the methods described herein. Statins include, but are not limited to, PRAVACHOL® (pravastatin, Bristol-Myers Squibb); MEVACOR® (lovastatin, Merck); ZOCOR® (simvastatin, Merck); LESCOL® (fluvastatin, Novartis); LIPITOR® (atorvastatin, Parke-Davis); CRESTOR® (rosuvastatin, Astra-Zeneca); and ADVICOR® (lovastatin plus extended release Niacin, Kos Pharmaceutical). In some embodiments, the methods described herein can include measuring the fasting levels of low-density lipoprotein (LDL) cholesterol, and administering a cholesterol-lowering agent when LDL cholesterol levels exceed 130 mg/dL. The treatment can be administered to lower levels of LDL cholesterol, e.g., to lower the LDL cholesterol level to below 100 mg/dL.

In some embodiments, the methods described herein include the administration of an anti-inflammatory agent. Anti-inflammatory agents that can be used in the methods described herein include, but are not limited to, alclofenac; aldlometasone dipropionate; algestone acetonide; alpha arnylase; amcinafal; amcinafide; amfenac sodium; amiprilose hydrochloride; anakinra; anirolac; anitrazafen; apazone; balsalazide disodium; bendazac; benoxaprofen; benzydamine hydrochloride; bromelains; broperamole; budesonide; carprofen; ciclofenac; cintazone; cliprofen; clobetasol propionate; clobetasone butyrate; clopirac; cloticasone propionate; cormethasone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; flufenamic acid; flumizole; flunisolide acetate; flunixin; flunixin meglumine; fluocortin butyl; fluorometholone acetate; fluquazone; flurbiprofen; fluretofen; fluticasone propionate; furaprofen; furobufen; halcinonide; halobetasol propionate; halopredone acetate; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lomoxicam; loteprednol etabonate; meclofenamate sodium; meclofenamic acid; meclorisone dibutyrate; mefenamic acid; mesalamine; meseclazone; methylprednisolone suleptanate; morniflumate; nabumetone; naproxen; naproxen sodium; naproxol; nimazone; olsalazine sodium; orgotein; orpanoxin; oxaprozin; oxyphenbutazone; paranyline hydrochloride; pentosan polysulfate sodium; phenbutazone sodium glycerate; pirfenidone; piroxicam; piroxicam cinnamate; piroxicam olamine; pirprofen; prednazate; prifelone; prodolic acid; proquazone; proxazole; proxazole citrate; rimexolone; romazarit; salcolex; salnacedin; salsalate; salycilates; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triclonide; triflumidate; zidometacin; glucocorticoids; and/or zomepirac sodium.

In some embodiments, the anti-inflammatory agent is aspirin. For example, the methods can include advising a subject to take about 81 mg of aspirin per day.

Hypertension also increases risk of adverse coronary events as a result of direct vascular injury, increased left ventricular mass, and myocardial oxygen demand. Lowering blood pressure reduces the risk of death, stroke, heart failure, myocardial infarction, and other vascular events, particularly in older patients with systolic hypertension. Thus, the methods described herein can include the administration of anti-hypertensive treatments to lower blood pressure to a desired level. In subjects with early stage atherosclerosis diagnosed by the methods described herein, blood pressure should ideally be less than 140/90 mm Hg. For subjects who also have diabetes, heart failure, or renal failure, lowering the blood pressure still further to less than 130/85 mm Hg is desirable. Anti-hypertensive treatments include, but are not limited to, administration of beta blockers, long-acting calcium channel blockers, or peripheral vasodilators, angiotensin-converting enzyme inhibitors, and angiotensin receptor blockers (which are preferred where left ventricular systolic dysfunction is present, or where the subject is otherwise at high risk) (The Heart Outcomes Prevention Evaluation Study Investigators. N. Engl. J. Med., 342:145, (2000)).

Long-acting calcium channel blockers include, but are not limited to, amlodipine, felodipine, extended release nifedipine, isradipine, nisoldipine, extended release nicardipine and diuretics Beta-adrenergic blocking agents include, but are not limited to, propranolol (Inderal®), atenolol (Tenormin®), acebutolol (Sectral®), and pindolol (Visken®).

Peripheral vasodilators include, but are not limited to, hydralazine (Apresoline®), isoxuprine (Vasodilan®), and minoxidil (Loniten®).

Angiotensin-converting enzyme inhibitors (ACE inhibitors), which act by inhibiting the production of angiotensin II, include, but are not limited to, captopril (Capoten®), benazepril (Lotensin®), enalapril (Vasotec®), and quinapril (Acupril®). Angiotensin II receptor antagonists include, but are not limited to, losartan (Cozaarg), candesartan (Atacand®), irbesartan (Avapro®), telmisartan (Micardis®), valsartan (Diovan®) and eprosartan (Teveten®).

An effective amount is a dosage sufficient to provide a medically desirable result. The effective amount will vary with the therapeutic agent selected, the age and physical condition of the subject being treated, the severity of the condition being treated, the duration of the treatment, the nature of the concurrent therapy (if any), the specific route of administration and like factors within the knowledge and expertise of the health practitioner.

Kits

The present invention also provides kits that are useful in carrying out the present invention. For example, a kit could easily be assembled for use in total CRP capture and release/concentration. In some embodiments, the kit includes instructions and vials of the dry reagents used in steps 1-6 of Part I in Example 6. For example, the kit may include a calcium supplementation buffer, e.g., 4 mmol/L $CaCl_2$ in a buffer, e.g., Tris-saline (60.3 mmol/L Tris HCl, 39.7 mmol/L Tris base, pH 8.0; 200 mmol/L NaCl) for calcium supplementation of the serum sample (as described in Part I, step 1); a rinse buffer, e.g., Tris-saline with 2 mmol/L $CaCl_2$, for rinsing unbound materials off of CRP-bound phosphorylcholine (PC) beads (as described in Part I, step 4), and release buffer (20 mmol/L $Na_2EDTA$, 1.5 mol/L KCl in Tris-saline) for the release and concentration of total CRP forms (as described in Part I, step 5). The kit can also include a vial of PC beads (e.g., as described in Part I, step 2), e.g., for a defined number of assays. The kit could also include microcentrifuge tubes for the convenience of the user.

Animal Model

Also described herein (e.g., in Example 1) is an animal model of accelerated atherogenesis. Although the experiments described herein use a rat, one of skill in the art will appreciate that other animals, e.g., mammals such as lagomorphs, dogs, and other rodents such as mice, can also be used.

In the animal model described herein, the process of wall lipid accumulation and associated serum markers is compressed into a 12-day hypertension-induction period, promoting the visualization of kinetic curves that might be difficult to appreciate in a more chronic pathologic process, and at the same time allowing temporal associations to be drawn between changing patterns of proinflammatory serum markers and the earliest, pre-monocytic stages of atherosclerosis. The data described herein indicate that the rising levels of mCRP and oxLDL provide serum markers for early neutral lipid accumulation in the arterial wall matrix.

Another useful feature of the animal model is the ability to compress the duration of the lipid clearance process to less than 24 days following the hypertension-induction phase, most simply through a post-induction low-fat/low-sodium diet that could allow associations to be drawn with serum markers of this process as well. The post-induction low-fat/low-sodium diet removes the atherogenic driving forces (elevated levels of dietary cholesterol and sodium) and allows monocytes that arrived at the end of the induction phase to clear oxLDL, a primary inciting molecule of atherogenic pathology, from the arterial matrix. Serum markers associated with the clearance phase would include declining levels of serum oxLDL and mCRP, but might also include declining markers of activated monocytes (foam cells), such as CD36. These same markers could also be used to monitor the effectiveness of therapeutic agents to hasten the natural clearance process, such as antihypertensive agents (e.g., calcium channel blockers or ACE-1 inhibitors). A quicker return to pre-induction blood pressure levels would theoretically more quickly dampen the hypertension driving force counteracting the monocytic clearance process.

The invention is further described in the following examples, which do not limit the scope of the invention described in the claims.

EXAMPLES

Example 1

Animal Model of Induced Hypertension and Atherosclerosis

This example describes the generation of an animal model of atherosclerotic lesions, which was used to characterize correlations between certain proinflammatory serum markers and histopathologic changes in the coronary walls with rising blood pressure.

Rapid (12-day) induction of early stage atherosclerotic lesions in the Dahl sodium-sensitive (Dahl S) rat requires a conditioning period (through early adolescence) on a high-cholesterol/low-sodium diet followed by a relatively sudden increase in blood pressure brought by the introduction of 8% dietary NaCl in a high-cholesterol/high-sodium diet. This conditioning both diminishes the elastic fiber concentration of the coronary vessels and sets up the animals for rapid accumulation of arterial wall neutral lipid (within eight days) following initiation of the high-cholesterol/high-sodium diet.

Animals, Vascular Conditioning/Preconditioning, and Hypertension Induction

The study design is an abbreviated version of that previously described (Kiefer et al., Circulation, 106:2486-2490 (2002)), in which the animals were conditioned on the high-cholesterol/low-sodium diet from weaning until 12 weeks of age, and then switched to the high-cholesterol/high-sodium diet for 12 days to induce a hypertensive state. A total of 77 Dahl SS/JrHsd male rats (Harlan Sprague Dawley, Indianapolis, Ind.) were used in three studies of the 12-day hypertension induction period: 42 for serum and histologic analysis (sampling 6-7 animals for each analysis at two day intervals); 18 for blood pressure readings; and 17 for daily caloric intake and weight change from baseline. An additional six animals were unconditioned to age 12 weeks (low-cholesterol/low-sodium diet) to control to evaluate the effect of the high-cholesterol component of the diet on levels of sICAM-1 and on the monocyte index (see Examples 2 and 4).

Test Diets

The high-cholesterol/low-sodium (conditioning) diet was modified from the purified Basal Diet™ 5755 (No. 56257, Purina Mills Test Diet, Richmond, Ind.) and included 8.5% coconut oil, 1.5% corn oil, 1.5% cholesterol, 0.5% sodium cholate, 0.15% DL-methionine, 0.4% NaCl, and 100 mg/kg zinc in addition to the standard sucrose/casein/vitamin-mineral base, and provided $4.13 \times 10^3$ kcal/kg energy (approx. 18% protein, 25% fat, 57% carbohydrates). The high-cholesterol/high-sodium diet (No. 29163, Purina Mills Test Diet) differed from the conditioning diet only in having higher concentrations of sodium (8.0% NaCl) and coconut oil (10.0%), no corn oil, and 21 mg/kg zinc, providing $3.83 \times 10^3$ kcal/kg energy (approx. 19% protein, 27% fat, 54% carbohydrates). The oil and zinc differences were found necessary to prevent skin problems in the preadolescent animals. The low-cholesterol/low-sodium diet was modified from the Basal Diet™ 5755 (No. 52876, Purina Mills Test Diet) by reduction of NaCl to 0.4%.

Blood Pressure

For the 18 animals reserved for tracking blood pressure changes over the course of the induction period, systolic and diastolic pressures and heart rate were measured using a plethysmographic tail-cuff system (No. XBP1003, Kent Scientific Corp., Torrington, Conn.). These animals were acclimated to the blood pressure measurement procedure for two sessions in the week prior to the beginning of the induction period. Two or more equilibrated (consistent slope) readings were taken as indicating that the tail had been optimally warmed, and the pressure with the better-resolved heart rate was recorded.

Results:

The change at 12 weeks of age from a high-cholesterol/low-sodium to high-cholesterol/high-sodium diet resulted in a phase of adjustment for the rats. Daily caloric intake and variation from baseline body weight are presented in FIG. 1. Initially, there was a decrease in caloric intake with an associated weight loss, although the sodium intake rose immediately because of the 20-fold increase in dietary NaCl concentration. By day 6, mean caloric intake had returned to stabilize at 12% below baseline (81.2 vs. 92.3 kcal/day), bringing a mean sodium intake approximately 21-fold higher than baseline (667 vs. 32 mg/day). Mean body weight slowly recovered from its nadir at day 4 (5.3% below baseline) to reach 2% below baseline by the end of the induction period. Water intake on the high-sodium diet immediately increased threefold, from a mean of 37.5 (SD 3.6) ml/day for the week preceding the induction period to 115.2 (SD 10.5) ml/day for the 12-day induction period.

Figure 2:
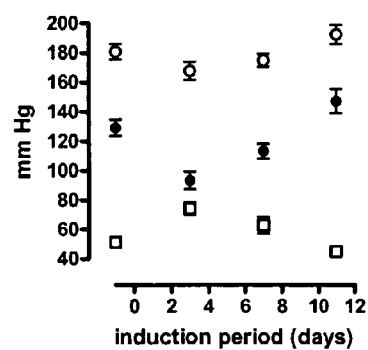
FIG. 2 is a graph illustrating blood pressure changes over the twelve day induction period of FIG. 1. ○, mean (SE) systolic pressure. ●, mean (SE) diastolic pressure. □, mean (SE) pulse pressure. Single group, N=18.

Blood pressure changes were associated with both the rising sodium intake and declining body weight (FIG. 2). The mean weight loss over the first three days, 5.1% of baseline weight, was associated with a fall of 35.9 mm Hg in mean diastolic pressure. In humans, a weight loss of ≧5% over 6 months is associated with a fall in diastolic pressure of 11.6 mm Hg (Wassertheil-Smoller et al., Arch Intern Med., 152:131-136 (1992)). Mean systolic pressure evidenced a smaller fall (13.1 mm Hg) during the first three days, with the result that mean peripheral pulse pressure (systolic-diastolic) increased significantly. The elevated pulse pressure began to decline after day 3, but continued to remain significantly above baseline through day 7 at least. Systolic/diastolic pressure did not rise above baseline until about nine days into the induction period.

Analysis:

These data demonstrate that the abbreviated protocol can be used to generate a reliable animal model of hypertension.

Example 2

Temporal Correlations of Proinflammatory Serum Markers sICAM-1 and LDL/oxLDL with Arterial Wall Neutral Lipid Accumulation The experiments in this example evaluated the correlations between induced hypertension, levels of certain proinflammatory markers, and arterial wall neutral lipid accumulation in the animal model described in Example 1.

Serum Analysis

For the 42 animals designated to provide data for serum analyte changes over the induction period, a blood sample of 1.5 ml (7% total blood volume) was collected from all 42 animals at day 0, and a second sample of 6.0 ml was collected as part of the euthanasia procedure for groups of 6-7 every other day (days 2 through 12). Blood samples were collected by retroorbital puncture to minimize hemolysis, then processed and frozen at −70° C. until use.

Six animals were unconditioned to age 12 weeks (low-cholesterol/low-sodium diet) to control for the effect of the high-fat component of the diet on levels of sICAM-1.

sICAM-1

Concentrations of sICAM-1 were determined by a quantitative sandwich enzyme immunoassay technique (Quantikine® Rat sICAM-1 (CD54) Immunoassay, No. RIC100, R&D Systems, Inc., Minneapolis, Minn.).

Total LDL and Oxidized LDL

Total LDL was measured directly by an automated assay (SYNCHRON LX® System, Beckman Instruments, Inc., Brea, Calif.), which is based on selective detergent solubilization of cholesterol from LDL particles, releasing cholesterol to be enzymatically coupled to a chromogenic substrate. Estimation of peroxidized lipids in circulating LDL followed the method for measurement of baseline diene conjugation (LDL-BDC) (Ahotupa et al., Clin Biochem., 29:139-144 (1996)), wherein the concentration of diene double bonds in LDL fatty acids (mainly linoleic acid) is measured spectrophotometrically after their isolation from LDL particles, the particles having been specifically and completely precipitated from serum with buffered heparin (Wieland and Seidel, J. Lipid. Res., 24:904-909 (1983)). Artifactual oxidation of LDL during sample preparation is prevented by the addition of EDTA.

Histomorphometry

As previously described (Kiefer et al., (2002) supra), hearts were frozen, cross-sectioned (10 μm) 5 mm from the apex, and stained for neutral lipids in the arterial wall (Oil Red O) or for the presence of monocytes adherent to the endothelium (hematoxylin-eosin) (see Example 4, below), focusing on the two major right posterior descending arteries and the interventricular coronary artery.

Arterial wall lipid density was measured by densitometry, as described (Kiefer et al., (2002) supra), with results expressed as net optical density (OD). For each heart, the coronary vessel cross-section at 5 mm from the apex with the highest lipid density was chosen as the index vessel in calculating the group mean.

Statistical Analysis

All measured parameters (caloric/sodium intake, body weight change, blood pressure, serum markers, and histomorphometry) were plotted as a function of time for the hypertension induction period, and are presented as means with standard error bars. Where indicated, statistical assessments were made of group mean differences in serum analytes or endothelium-adherent monocytes during the course the 12-day induction period. Because group mean values for any day except day 0 were derived from independent groups of animals, the unpaired t test was usually used. The exception was the analysis of oxLDL mean differences between days 0 and 2 of the induction period, where blood samples from the same group of animals were used. For this paired or repeated comparison alone, the analysis of variance test for overall differences over time was used to take into account variation over time and residual variability in these group mean differences (Wallenstein et al., Circ. Res., 1980; 47:1-9 (1980)). For all group mean comparisons, a P value<0.05 was considered significant.

Results:

sICAM-1

Figure 3:
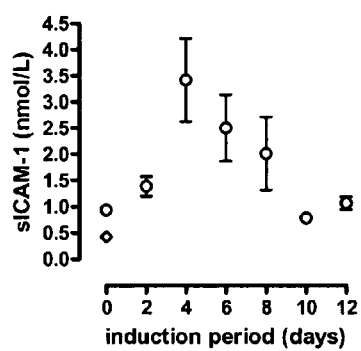
FIG. 3 is a graph illustrating changes in soluble intercellular adhesion molecule-1 (sICAM-1) levels over the twelve day induction period. ○, mean (SE) serum level of sICAM-1; six groups, N=7 each (same group for days 0 and 2). ◇, mean (SE) level of sICAM-1 for non-preconditioned animals at age 12 weeks; N=6.

The level of sICAM-1 rapidly increased at the beginning of the induction period, peaking by day 4 at three- to four-fold over baseline (P<0.01) and returning to baseline by day 10 (FIG. 3). FIG. 3 also depicts the sICAM-1 baseline level of unconditioned animals at age 12 weeks, which at 0.428 nmol/L was significantly lower than that of the conditioned animals (0.937 nmol/L) at the same age (12 weeks, day 0) ($P<0.0001$).

oxLDL

Figure 5:
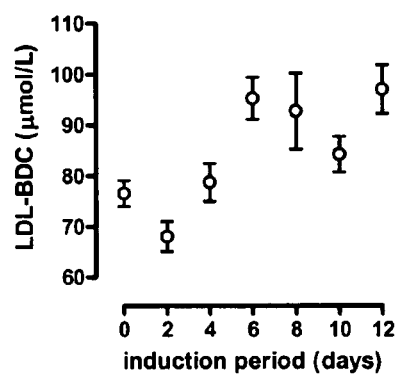
FIG. 5 is a graph illustrating changes in serum oxidized low-density lipoprotein (LDL) levels over the twelve day induction period. ○, mean (SE) oxidized LDL, measured as LDL-baseline diene conjugate (LDL-BDC); six groups, N=7 each (same group for days 0 and 2).

The level of oxLDL initially fell 11 to 14%, reaching a nadir on about day 2 (not significant vs. day 0), and then rose above baseline, plateauing by day 6 at 24% over baseline ($P<0.005$) (FIG. 5). For each of the groups sampled at days 0, 2, 4 and 6, three representative sera were selected that covered the entire range of oxLDL values for each of the four days. There was no significant change in direct total LDL mean values for these four subsets over the six days (range 4.665 to 5.685 mmol/L). Moreover, there was no correlation of oxLDL with total LDL values for any given serum.

Pooled Neutral Lipid

Figure 6:
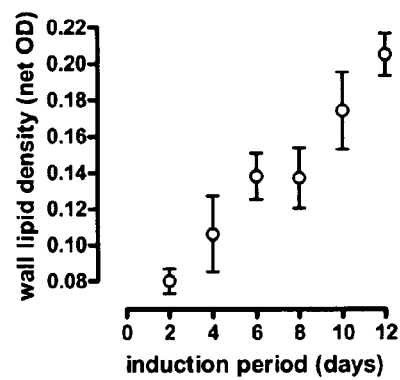
FIG. 6 is a graph illustrating the accumulation of pooled neutral lipid within the extracellular matrix over the twelve day induction period. ○, mean (SE) net density of Oil Red O stain within the arterial wall; N=7, each group. No pooled lipid was observed in any of the animals sampled at day 2.

Pooled neutral lipid in the arterial wall accumulated at a constant rate from days 2 through 12 of the induction period with the exception of a pause from days 6 to 8 (FIG. 6). No pooled lipid was observed at day 2. As a general histologic observation, the distribution of the stained pooled lipid within the arterial wall was limited to one or more foci comprising less than 15% of the vessel's cross-sectional area for wall lipid densities <0.15, and was distributed over the entire intima cross-section for densities >0.19. Red stained areas within the arterial walls indicate the presence of neutral lipid. The accumulation of neutral lipid corresponded with a more rounded vessel cross-section, consistent with a destruction of elasticity (Bobryshev and Lord, Atherosclerosis, 142:121-131 (1999)).

Analysis:

The results support our previous conclusion that LDL retention within the arterial wall per se is not sufficient to initiate atherogenesis (Kiefer et al., (2002) supra), but that increased blood pressure is required to shift the pathological process to histologically observable levels. Temporally correlating with the immediate rise in pulse pressure is the rise in sICAM-1, which then dissipates in correlation with the decline in pulse pressure to baseline. This would imply that endothelial cells are more responsive to elevations of pressure differential than to elevations of systolic or diastolic pressure in absolute terms.

The case can be made that elevated pulse pressure also drives the rise in oxLDL, but more slowly than it does for sICAM-1. The level of oxLDL rises above its baseline by about day 5, thus about five days after pulse pressure begins its ascension, but four days before systolic/diastolic pressure begins to rise above its baseline on about day 9. This five-day delay in the rise of circulating oxLDL might be explained by the more time-consuming logistics involved in oxidizing LDL and bringing it from the reaction site, the wall matrix, to the circulation. Further, increased pressure on the arterial wall (initially pulse pressure) could slow down the diffusion time between the two compartments (arterial wall and circulation). Thus, LDL retention time within the proteoglycan matrix would increase, allowing oxidative processes to proceed further towards completion and resulting in a reequilibration of oxLDL in both compartments to higher levels.

Of special interest to the current application are the reequilibrations of the serum markers mCRP and then oxLDL in the pre-monocytic phase of the developing atherosclerotic pathology—days 0 to 8 of the animal model induction phase (see Example 4). Elevation of oxLDL in the arterial matrix (presumably represented by rising serum oxLDL levels) is likely to positively influence the recruitment and retention of monocyte/macrophages (Quinn et al., (1987) supra). Thus, the rising slope of serum oxLDL would mark a pathologic transition to a theoretically less easily reversible stage of the disease.

Example 3

Temporal Correlations of mCRP Levels with Arterial Wall Neutral Lipid Accumulation The experiments in this example evaluated the correlations between induced hypertension, initial atherosclerotic changes, and serum monomeric CRP levels in the animal models described in Example 1.

Serum Analysis

For the 42 animals designated to provide data for serum analyte changes over the induction period, a blood sample of 1.5 ml (7% total blood volume) was collected from all 42 animals at day 0, and a second sample of 6.0 ml was collected as part of the euthanasia procedure for groups of 6-7 every other day (days 2 through 12). Blood samples were collected by retroorbital puncture to minimize hemolysis, then processed and frozen at −70° C. until use.

Total CRP and Monomeric CRP

For estimations of free monomeric CRP and total CRP (monomeric+dimeric forms), which are what remains after dissociation of the pentameric forms in the rat), CRP was first absorbed from serum (500 µL of a 1% dilution) by phosphoryl choline (PC) immobilized onto beaded agarose (50 µL solution, binding capacity 5 to 11 µg CRP/µL) (Pierce Biotechnology, Rockford, Ill.), in the presence of 1 mmol/L $CaCl_2$. The excess binding capacity (minimum 3500-fold for the highest CRP concentrations expected) was designed to assure complete recovery, and evaluation of the method indicated as much (no CRP was isolated from PC-depleted serum). The entire isolate was electrophoresed under non-reducing conditions (10% Laemmli/SDS-PAGE) on a mini-gel (Mini-PROTEAN®II, Bio-Rad Laboratories, Hercules, Calif.), blotted onto nitrocellulose (NitroME, 0.1 µm pore, Micron Separations, Inc., Westboro, Mass.), and stained with colloidal gold (Bio-Rad Laboratories). Positive identification of CRP in monomeric ($M_r$ 23.4 kDa) and dimeric ($M_r$ 49.0 kDa) bands was made both immunologically (goat anti-human CRP, #G-112-C, Fortron Bio Science Inc., Morrisville, N.C.) and by sequence analysis (Midwest Analytical, St. Louis, Mo.) of bands blotted to polyvinylidene fluoride (PVDF) (Immobilon™-$P_{SQ}$, Millipore Corp., Bedford, Mass.).

Gold-stained blots were analyzed by densitometry (Model GS-700, Bio-Rad Laboratories) and monomeric and dimeric CRP concentrations in each sample were interpolated from concurrently run human CRP standards (#30-AC05, Fitzgerald Industries International, Inc., Concord, Mass.) within the linear range of 3 to 27 ng/band. The total concentration of serum CRP was expressed as subunit molarity (rat subunit CRP=23,435 kDa) due to the uncertainty of the ratio of the various circulating multiples (pentamer, monomer, and possibly dimer). Total subunit concentration was taken to be the sum of the monomeric+dimeric concentrations. The monomeric bands revealed by SDS-PAGE were assumed to represent the sum of three monomers per captured native pentamer plus all free monomers in the original sample. The concentration of free monomeric serum CRP (mCRP), while thus not estimated directly, was taken to be reflected in the monomer/dimer ratio.

Statistical Analysis

Statistical analysis was performed as described in Example 2.

Figure 4:
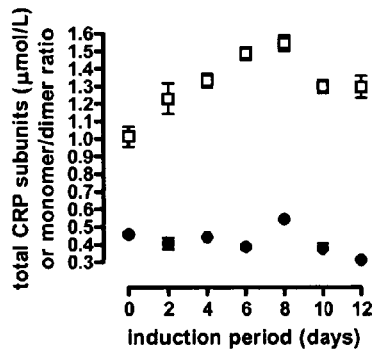
FIG. 4 is a graph illustrating changes in total serum CRP and CRP monomer/dimer ratio over the twelve day induction period. ●, mean (SE) total CRP. □, mean (SE) CRP monomer/dimer ratio. Five groups, N=7 each (same group for days 0 and 2); one group, N=6 (day 8).

Results:

Estimation of the relative concentration of free monomeric CRP relied on the existence of two covalently-linked subunits within the standard pentameric structure of the rat CRP, a feature unique to rats (Rassouli et al., J Biol. Chem., 267: 2947-2954 (1992)). Theoretically, the monomer/dimer band ratio on gel blots would be 1.5 if there were no free monomers in the serum sample. However, the measured mean baseline ratio (ratio prior to the induction period) was only 1.01 (FIG. 4, day 0). The monomer/dimer ratio increased immediately and steadily from day 0, plateauing by day 8 at 53% over baseline (P<0.0001 vs. day 0) and declining slightly thereafter to 28% over baseline (P=0.001 vs. day 0). The kinetics of this marker ratio thus correlated initially with the rising pulse pressure and then with the sustained increase (over baseline) of systolic/diastolic pressure. The CRP subunit total was generally unchanged or declining throughout the induction period with the exception of a spike on day 8 (>40% above days 6 or 10; $P \leq 0.001$).

Analysis:

These data illustrate that levels of mCRP rise in concert with the sudden increase in pulse pressure, but then re-equilibrate at a higher level in association with the elevation in systolic/diastolic pressure. As one hypothesis, this rise of mCRP in the absence of a discernable rise in total CRP occurs when elevated hemodynamic stress, associated with early atherosclerotic events, promotes apoptotic-mediated PC exposure on the endothelial surface. This allows capture of circulating native pentameric CRP, and the membrane-localized dissociation of the pentameric CRP to monomers. The monomers then reenter the circulation, where they can be detected by a method such as the one described herein, providing an early indication of the development of atherosclerotic processes.

Example 4

Appearance of Endothelium-adherent Monocytes

To further characterize correlations between histopathologic changes in the coronary walls with rising blood pressure, the accumulation of monocytes was evaluated in the animal model described in Example 1.

Six animals were unconditioned to age 12 weeks (low-cholesterol/low-sodium diet) to control for the effect of the high-cholesterol component of the diet on the monocyte index.

Histomorphometry

Hearts were prepared for coronary vessel monocyte counts as described above in Example 2. A quantitative index of endothelium-adherent monocytes was established by counting these cells in the three major coronary arteries at 2, 3, 4, and 5 mm from the apex (i.e., 12 cross-sections total). More than 10 adherent monocytes in any single vessel were counted as only 10. Thus, a maximum index of 120 attached monocytes was possible for any given heart.

Figure 8:
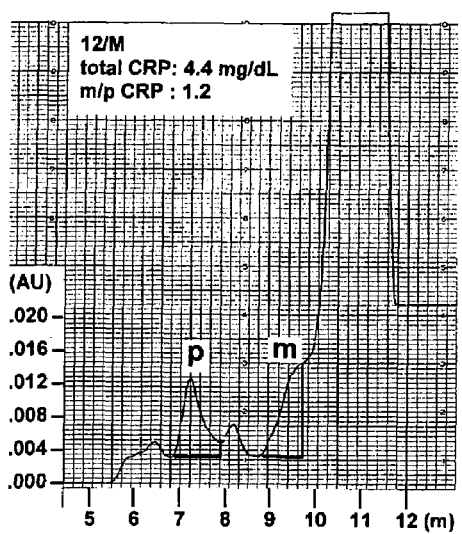
FIGS. 8 and 9 are graphs illustrating mCRP (peak at about 7.25 minutes) and pCRP (peak at about 9-9.5 minutes) levels in two human subjects, with a total CRP level of 5.5× the critical value (FIG. 8) or total CRP level of 18× critical value (FIG. 9).

Results:

As depicted in FIG. 8, a mean background of 3.43 (SD 2.23) endothelium-adherent monocytes in conditioned animals could be found in the 12 coronary cross sections used in calculating the monocyte index (day 2). This low-level monocyte background was significantly above the index of 0.83 (SD 0.41) for unconditioned animals (P<0.02). A transient but significant (P<0.05 vs. day 2) spike in the index on day 6 was followed by a return to baseline by day 8, and then a sustained rise extending to the end of the 12-day induction period. Foam cells in the arterial intima were not seen before the last day of the induction period. On day 12, two of the seven animals examined each revealed multiple foam cells in two or three of the twelve vessel cross-sections examined.

Figure 7:
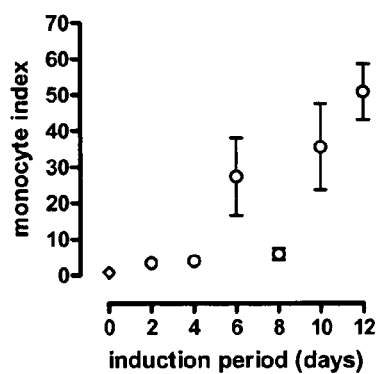
FIG. 7 is a graph illustrating changes in counts of coronary endothelium-adherent monocytes over the twelve day induction period. ○, mean (SE) count of endothelium-adherent monocytes (index described in Methods); N=7, each group. ◇, mean (SE) count for non-conditioned animals; N=6.

Analysis:

The brief spike in adherent monocytes at day 6 may be the response to an earlier transient expression of ICAM-1 on the endothelium, as suggested by the sICAM-1 peak at day 4 (see Example 2, FIG. 3). The low-level background of endothelium-adherent monocytes vs. unconditioned animals (FIG. 7) may reflect a low-level endothelial expression of ICAM-1 resulting from hyperlipidemia, as suggested by the elevation of sICAM-1 vs. unconditioned animals at age 12 weeks (FIG. 3). Low-level but significant elevations of sICAM-1 have been reported in normotensive patients with combined hyperlipidemia (hypercholesterolemia coincident with hypertriglyceridemia) (Kvasnicka et al., Sb. Lek., 102:473-477 (2001)).

Together with the data presented in Examples 1 and 2, these data indicate that there are at least two different driving forces operating in the present model of wall lipid accumulation: mechanical (elevated pulse pressure, days 0 to 8) and cellular (monocytes, days 8 to 12). In longitudinal clinical studies, pulse pressure has emerged as a risk factor for cardiovascular disease, with a relative risk highest for the youngest subjects (Thomas et al., J. Hypertens., 19:863-869 (2001); Fang et al., Blood Press., 9:260-266 (2000)). Pulse pressure also correlates slightly better than systolic pressure with large artery stiffness and endothelial dysfunction (Nigam et al., Am. J. Cardiol., 92:395-399 (2003)). In this regard, the animal model conforms to human pathophysiology.

Example 5

Calculation of Normal and Pathological Human mCRP Values

The rat mCRP data in Example 3 were presented as a ratio of the monomeric to dimeric form, as no direct measurements of mCRP in serum were conducted. In the rat model, the estimation of the relative concentration of free monomeric CRP relied on the existence of two covalently-linked subunits within the standard pentameric structure, a feature unique to rats among mammals (Rassouli et al., (1992) supra). Because of uncertainty of the ratio of the various CRP assemblies in serum (native pentamer, free monomer, and perhaps free dimer), total rat CRP concentrations (sum of monomer+ dimer concentrations) were expressed as subunit molarities. Given these uncertainties, some assumptions are necessary before estimating human mCRP concentration ranges in normal or subclinical pathologic states. These assumptions are as follows.

(a) subclinical pathologic changes in human ranges will simulate those in the experimental rat model. This is a reasonable assumption, based on the fact that when Dahl S rats remain on the hypertension induction diet until their death (up to 55 days later), post-mortem analysis indicates advanced atherosclerotic lesions, histologically similar to human Stary Stage III (see Kiefer et al., Circulation, 2002, 106:2486-2490, FIGS. 3-5). If one accepts the position that similar final pathologies in the rat and human can be extrapolated backward in time to similar initial subclinical pathologies, then this rat is a good model for human atherosclerosis, from subclinical stages through at least Stary Stage III;

(b) estimates of specific human mCRP levels will be proportionate to total human CRP levels in the same way that rat mCRP levels are proportionate to total rat CRP levels (see above); and, (c) mCRP at any detectable level is indicative of pathology.

The starting monomer:dimer ratio of 1.013 was significantly below the theoretical starting monomer:dimer ratio of 1.5. Thus, the change in monomer/dimer ratio [peak induction ratio, day 8 (1.545):pre-induction ratio, day 0 (1.013) =1.525] was used as the pathologic multiplier. Given the known total rat CRP concentration at day 0 (10.7 mg/L, all pentamer based on assumption (c) above), and the fact that the total CRP concentration remains relatively unchanged over 8 days, then the peak induction concentrations in the rat at day 8 would be 8.2 mg/L pentamer and 2.5 mg/L free monomer, yielding an estimated monomer:dimer ratio at day 8 of 2.262, and at day 0 of 1.5 (the theoretical zero free monomer ratio). Thus, the change in ratio would be 1.508 (2.262/1.5), which is close to the observed 1.525 found in the model.

Applying those figures to the normal human range of total CRP in serum for clinically non-pathologic states (1.26-1.97 mg/L), and taking into account assumptions (b) and (c), normal human mCRP levels would be estimated to be approximately zero, and ranges for subclinical/earliest stage atherosclerosis would be estimated at 0.3 to 0.5 mg/L (13-21 nmol/L). "Normal" (nonpathologic) human serum theoretically would have absolutely no free mCRP by the terms of assumption (c), above. Realistically, however, it is likely that there will always be an ultra-low (background) level of mCRP in circulation, resulting from constant low-level tissue damage, i.e., the normal wear-and-tear of human existence, such as bumps and physical exercise. In the previous paragraph, the peak induction (day 8) rat serum was estimated to have 8.2 mg/L pentamer and 2.5 mg/L free monomer, thus totaling 10.7 mg/L total CRP in circulation. Taking the rat mCRP/total CRP ratio at day 8 (2.5/10.7=0.23) as representing a subclinical pathologic state (minimal vascular pathology as indicated by histomorphometric data), and multiplying by the non-pathologic ("normal") range for total human CRP (1.26-1.97 mg/L), gives 0.23×1.26=0.29 mg/L at the low end, and 0.23× 1.97=0.45 mg/L of mCRP in serum at the high end of the range of normal values.

Example 6

Manual Method for C-Reactive Protein Capture and Release from Serum and Monomer/Pentamer Fractionation and Quantitation In this example, manual methods were used to measure the levels of CRP and mCRP in serum. This example describes a two-part method.

Part I (Total CRP Capture and Release/Concentration)

1. Serum samples were microcentrifuged (1 minute). 250 µL aliquots were diluted with 250 µL of 4 mmol/L $CaCl_2$ in Tris-saline (60.3 mmol/L Tris HCl, 39.7 mmol/L Tris base, pH 8.0; 200 mmol/L NaCl).

2. 50 µL phosphoryl choline bead slurry (product # 20307, Pierce Biotechnology, Inc., Rockford, Ill.) was microfuged, and supernatant was drained from pelleted beads with a flexible capillary such as a gel-loading pipet tip.

3. The calcium-supplemented, diluted sample (from step 1) was added to the microcentrifuge tube with the pelleted beads and platform-mixed (with maximum inclinations) at room temperature (approximately 22° C.) for 1 hour.

4. The bead-captured CRP was microfuged and beads were drained, then rinsed by adding 1 mL Tris-saline with 2 mmol/L $CaCl_2$ and platform-mixing for 5 minutes at room temperature. The beads were drained, and the rinse/drain was repeated twice more.

5. Total CRP was released from the beads with 25 µL of release buffer (20 mmol/L $Na_2EDTA$, 1.5 mol/L KCl in Tris-saline). Beads were stirred in the release buffer for 10 seconds every minute for a total of 10 minutes at room temperature, then microfuged, and the supernatant (containing released CRP) was drained into a holding microcentrifuge tube. Any residual CRP was released from the beads with another 25 µL of release buffer, repeating the 10-minute incubation. The second supernatant was pooled with the first in the holding tube.

6. The released CRP was microfuged to maximize isolation from residual beads which may have been carried across into the holding tube, and the supernatant was transferred to a second holding tube. This clean-up step was repeated twice more, and the final volume of released total CRP was measured. Generally, the final volume was about 40-50 µL, depending on losses incurred during steps 5 and 6.

Part II (HPLC Isolation of pCRP and mCRP; Calculation of mCRP:pCRP Ratio)

1. Mobile phase (83.3 mmol/L $Na_2HPO_4$, 16.7 mmol/L $NaH_2PO_4$, pH 7.45) was flowed through the HPLC system: pump (eg, Waters Associates, Inc. model 510 Solvent Delivery System, Millipore, Milford, Mass.); sample injector (e.g., Waters model U6K Universal Liquid Chromatograph Injector, Millipore); size exclusion column (e.g., Bio-Sil SEC 250-5, 7.8×300 mm, Bio-Rad Laboratories, Inc., Hercules, Calif.); detector (e.g., Waters model 484 Tunable Absorbance Detector, Millipore); and recorder (e.g., Fisher Recordall Series 5000 chart recorder, Houston Instrument, Austin, Tex.). Flow rate was gradually increased to 1.0 mL/minute (e.g., 0.1 to 1.0 mL/min in 0.1 mL/min increments every 30 seconds) to avoid compression of the column packing. Final column pressure was about 450-500 psi.

2. Absorbance of the mobile phase was equilibrated as it flowed through the detector. Energies were recorded at 215 nm through the sample and reference cells. The absorbance range was set to 1.0 absorbance units full scale (AUFS).

3. The chart recorder was equilibrated at 10 mV full scale, and the chart recorder pen position was set at 5% full scale.

4. 20 µL of gel filtration standards covering the CRP pentamer-monomer molecular weight range (i.e., 115,000-23, 000), such as the 670,000-1,350 set by Bio-Rad (catalog # 151-1901) were injected and the chart recorder was started. The peak absorbances of the standards were noted from the detector. The HPLC record was ended at 13 minutes and the precise pen distance was recorded on the chart.

5. The absorbance units full scale (AUFS) range on the detector was changed to 0.05-0.20, depending on the initial total CRP level (eg, CRP Ultraquant assay, Beckman Coulter, Inc.), using the 0.05 AUFS range for initial levels nearer the clinical critical value (8 mg/L).

6. 20 µL of the released total CRP sample (representing 20/50, or 40% of the initial serum aliquot of 250 µL, or 100 µL serum-equivalent) was injected and the chart recorder was started. The HPLC run was completed as in step 4. If the CRP peaks (step 8) were too small to determine a peak elution time or were off scale, the AUFS range was changed accordingly and a second 20 µL sample injected and run.

7. The chart rate (mm/minute) was calculated, as were the peak elution times of the standards and the CRP peaks. Standards generally eluted close to 6.24 minutes (SD 0.03) (670, 000), 7.86 minutes (SD 0.02) (158,000), 8.70 minutes (SD 0.01) (44,000), 10.00 minutes (SD 0.02) (17,000), and 11.43 minutes (SD 0.03) (1,350). The CRP pentamer eluted close to 7.25 minutes (SD 0.04), and the monomer from 8.98-9.69 minutes. The monomer peak had a characteristic long trailing edge at high concentrations.

8. Areas of pentamer and monomer peaks were calculated, and monomer peak area was divided by pentamer peak area to yield CRP mCRP:pCRP ratio.

Figure 9:
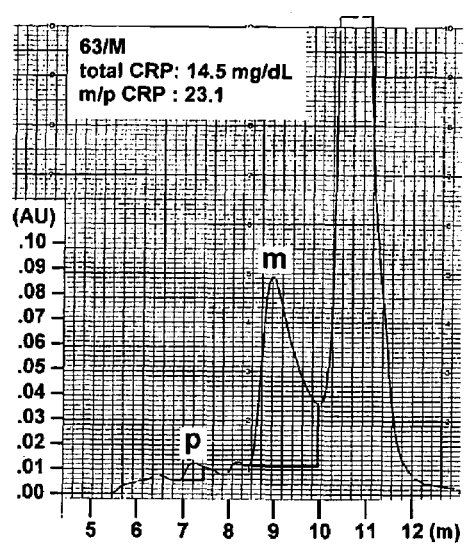

The results are shown in FIGS. 8 and 9, which display analyses of two human samples for monomer/pentamer CRP ratios by the method described in Example 6. Of the 20-30 samples that arrive daily at the Dept. of Hospital Labs, UMass Memorial Medical Center, with requests for total CRP level, these two were subsequently re-tested to discern the robustness of the mCRP:pCRP ratio over a wide range of critical values.

FIG. 8 is the analysis of a 12-year-old male with a total CRP of 4.4 mg/dL, which is about 5.5 times the critical value (0.8 mg/dL). The pentamer (p) and monomer (m) peaks eluted at about 7.25 and 9.5 minutes (x axis), respectively, and the mCRP:pCRP ratio of the peak areas indicated on the chromatograph was 1.2. Absorbance units at 215 nm are indicated on the y axis. FIG. 9 is the analysis of a 63-year-old male with a total CRP of 14.5 mg/dL (18 times the critical value). The mCRP:pCRP ratio here was 23.1.

Taken together, these results suggest that as the total CRP level rises arithmetically, the mCRP:pCRP ratio rises geometrically. These results demonstrate that the mCRP:pCRP ratio behaves as expected on theoretical grounds, i.e., that the ratio is a real measure of tissue damage. By extrapolation to the types of samples expected from typical subjects to be screened for early-stage atherosclerosis, the same sort of mCRP:pCRP relationship would be expected, even though total CRP values would be subcritical and the y axis would correspondingly display a 5-50 fold lower absorbance range.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing a subject with early stage atherosclerosis, the method comprising:
    providing a sample from a subject suspected of having early stage atherosclerosis;
    contacting the sample with phosphorycholine (PC), under conditions sufficient for C-reactive protein (CRP) binding to the PC to occur;
    isolating the PC-bound CRP;
    fractionating the PC-bound CRP based on size;
    determining a level of one or more of the fractions of CRP in the sample;
    and
    comparing the level of one or more of the fractions of CRP in the sample with a predetermined value,
    wherein the presence of the one or more fractions of CRP in the sample at a level above that of the predetermined value indicates that the subject has early stage atherosclerosis.

2. The method of claim 1, wherein the sample comprises a bodily fluid.

3. The method of claim 2, wherein the bodily fluid is serum.

4. The method of claim 1, wherein the subject has one or more risk factors selected from the group consisting of elevated serum LDL-cholesterol levels; elevated pulse pressure; family history; smoking history; diabetes mellitus; dyslipidemia; hypertension; a family history of premature atherosclerosis; and hyperhomocystinemia.

5. The method of claim 1, wherein the subject is an adolescent human, a preadolescent human, or a human in late childhood.

6. The method of claim 1, wherein the subject has one of intermittent claudication and rest pain.

7. The method of claim 1, wherein the subject has neither intermittent claudication nor rest pain.

8. The method of claim 1, wherein the predetermined value is a level of PC-bound CRP in an age-matched, normal, healthy control.

9. The method of claim 1, further comprising administering a treatment for atherosclerosis to the subject where the one or more fractions of CRP is present in the sample at a level above that of the predetermined value.

10. The method of claim 9, wherein the treatment is selected from the group consisting of diet modification; exercise modification; administration of an antiplatelet agent; administration of a cholesterol lowering agent; and administration of an anti-hyertensive agent.

11. The method of claim 1, wherein the PC is conjugated to a bead.

12. The method of claim 11, wherein the bead is an agarose bead.

13. The method of claim 1, wherein the PC is coated on a microtiter well.

14. The method of claim 1, wherein a size-exclusion fractionation is performed using high performance liquid chromatography.

15. The method of claim 1, further comprising determining the level of total CRP in the sample and calculating the ratio of the one or more fractions to the total CRP, wherein the ratio indicates whether the subject has early stage atherosclerosis.

* * * * *

UNITED STATES PATENT AND TRADEMARK OFFICE
CERTIFICATE OF CORRECTION

PATENT NO. : 7,482,174 B2  Page 1 of 1
APPLICATION NO. : 11/220818
DATED : January 27, 2009
INVENTOR(S) : Charles R. Kiefer et al.

It is certified that error appears in the above-identified patent and that said Letters Patent is hereby corrected as shown below:

Col. 22, in claim 10, line 4, delete "hyertensive" and insert -- hypertensive --.

Signed and Sealed this

Seventh Day of April, 2009

JOHN DOLL
*Acting Director of the United States Patent and Trademark Office*